United States Patent [19]
Hoffman

[11] Patent Number: 5,215,912
[45] Date of Patent: Jun. 1, 1993

[54] MONOCOT SEED STORAGE PROTEINS IN DICOTS

[75] Inventor: Leslie M. Hoffman, Madison, Wis.

[73] Assignee: Lubrizol Genetics, Inc., Wickliffe, Ohio

[21] Appl. No.: 393,834

[22] Filed: Aug. 14, 1989

Related U.S. Application Data

[63] Continuation of Ser. No. 902,224, Aug. 29, 1986, abandoned.

[51] Int. Cl.$^5$ .................. C12N 5/00; C12N 15/00; C12P 21/00; C12P 21/04
[52] U.S. Cl. .................. 435/240.4; 435/69.1; 435/70.1; 435/172.3; 935/67; 800/255; 800/DIG. 70
[58] Field of Search .................. 435/69.1, 69.8, 70.1, 435/172.3, 240.4, 320.1; 536/27; 800/205, 255, DIG. 70

[56] References Cited

FOREIGN PATENT DOCUMENTS 0142924 5/1985 European Pat. Off. .

OTHER PUBLICATIONS

Marks et al. 1985. J. Biol. Chem. 260(30):16451–16459.
Marks et al. 1982. J. Biol. Chem. 257:9976–9983.
Sengupta-Gopalan et al. 1985. Proc. Natl. Acad. Sci. USA 82:3320–3324.
Adang et al., 1985. Chem. Abstr. 103(9): #66080c.
Gelvin et al. 1985. Mol. Gen. Genet. 199:240–248.
Wilson et al. 1984. J. Mol. Evol. 20:330–340.
Lewin, B. 1987. Genes, Third edition, John Wiley & Sons: New York.
Keith et al. 1986. EMBO J 5(10):2419–25.
Lamppa et al. 1985. Nature 316:750–752.
Pedersen et al. (1982) Cell 29:1015–1026.
Spena et al. (1982) EMBO J. 1:1589–1594.
Spena et al. (1983) J. Mol. Biol. 169:799–811.
Pedersen et al. (1986) J. Biol. Chem. 261:6279–6284.
Sumner-Smith et al. (1985) Nucl. Acids Res. 13:3905–3916.
Scheets et al. (1985) Plant Sci. Lett. 37:221–225.
Forde et al. (1981) Nucl. Acids. Res. 9:6689–6707.
Forde et al. (1983) FEBS Lett. 162:360–366.
Goldsbrough et al (1986) Mol. Gen. Genet. 202:374–381.
Rochester et al. (1986) EMBO J. 5:451–458.
Ellis et al. (1987) EMBO J. 6:11–16.
Geraghty et al. (1981) Nucl. Acids. Res. 9:5163–5174.
Loenen and Brammar (1980) Gene 20:249–259.
Rafalski et al. (1984) EMBO J. 3:1409–1415.
Forde et al. (1985) EMBO J. 4:9–15.
Matzke et al (1984) EMBO J. 3:1525–1531.
Gelvin (1987) Plant Mol. Biol. 8:355–359.
Shaw et al. (1984) Nucl. Acids Res. 12:6031–6041.
Rubin (1986) Mol. Gen. Genet. 202:312–320.
Hepburn and White (1985) Plant Mol. Biol 5:3–11.

*Primary Examiner*—David T. Fox
*Attorney, Agent, or Firm*—Greenlee and Winner

[57] ABSTRACT

The present invention discloses dicot cells containing monocot seed storage protein. Construction of genes encoding monocot seed storage proteins which are expressible in dicot cells and transformation of such genes into plant cells is also taught. Furthermore, methods and DNA molecules useful for producing plant cells containing monocot seed storage proteins are also disclosed. The invention is exemplified by combination of a 15 kD zein structural gene from *Zea mays* gene with a promoter and a polyadenylation site derived from a *Phaseolus vulgaris* phaseolin gene.

4 Claims, 2 Drawing Sheets

MONOCOT SEED STORAGE PROTEINS IN DICOTS

This application is a continuation, of application Ser. No. 902,224, filed Aug. 29, 1986, now abandoned.

FIELD

The present invention is in the fields of genetic engineering and plant husbandry, and especially provides a means for producing monocot seed storage proteins in a dicot by transforming a dicot to contain a monocot seed storage protein structural gene under control of a non-monocot promoter. Also provided are plant-transforming prokaryotic plasmid vectors carrying such dicot-expressible monocot seed storage genes and plant cells transformed by such a vector.

BACKGROUND

Overview of Agrobacterium

Reviews of Agrobacterium-caused disease, plant transformation, genetic engineering, and gene expression include those by, or found in, Merlo D J (1982) Adv. Plant Pathol. 1:139-178; Ream L W and Gordon M P (1982) Science 218:854-859; Bevan M W and Chilton M-D (1982) Ann. Rev. Genet. 16:357-384; Kahl G and Schell J (1982) *Molecular Biology of Plant Tumors;* Barton K A and Chilton M-D (1983) Meth. Enzymol. 101:527-539; Weissbach A and Weissbach H, eds. (1986) Meth. Enzymol. 118 (see especially Rogers S G et al., pp. 627-640); Depicker A et al. (1983) in *Genetic Engineering of Plants: an Agricultural Perspective*, eds: Kosuge T et al., pp. 143-176; Caplan A et al. (1983) Science 222:815-821; Hall T C et al., European Patent application 126,546; and Binns A N (1984) Oxford Surveys Plant Mol. Cell Biol. 1:130-160; Hall T C (1985) Oxford Surveys Plant Mol. Biol. 2:329-338; Hooykaas P J J and Schilperoort R A (1985) Trends Biochem. Sci. 10:307-309; Thomas T L and Hall T C (1985) Bioassays 3:149-153; Puhler A, ed. (1983) *Molecular Genetics of the Bacteria-Plant Interaction;* and Schilperoort R A (1984) in *Efficiency in Plant Breeding* (Proc. 10 th Congr. Eur. Assoc. Res. Plant Breeding), eds: Lange W et al., pp. 251-285.

Transformation of Plants by Agrobacterium

Plant cells can be transformed by Agrobacterium by several methods well known in the art. For a review of recent work, see Syono K (1984) Oxford Surveys Plant Mol. Cell Biol. 1:217-219. Inoculation of leaf disks is particularly advantageous (Horsch R B et al. (1985) Science 227:1229-1231).

The host range of crown gall pathogenesis may be influenced by T-DNA-encoded functions such as onc genes (Hoekema A et al. (1984) J. Bacteriol. 158:383-385; Hoekema A et al. (1984) EMBO J. 3:3043-3047; Buchholz W C and Thomasshow M F (1984) 160:327-332; Yanofsky M (1985) Mol. Gen. Genet. 201:237-246) Vir genes also affect host range (Yanofsky, supra).

Genes on the Transformation-Inducing Plasmids

The complete sequence of the T-DNA of an octopine-type plasmid found in ATCC 15955, pTi15955, has been reported (Barker R F et al. (1983) Plant Mol Biol. 2:335-350) as has the $T_L$ region of pTiAch5 (Gielen J et al. (1984) EMBO J. 3:835-846). Published T-DNA genes do not contain introns. Sequences resembling canonical eukaryotic promoter elements and polyadenylation sites can be recognized.

The ocs gene encodes octopine synthase (lysopine dehydrogenase). Koncz C et al. (1983) EMBO J. 2:1597-1603 provide a functional analysis of ocs. Dhaese P et al. (1983) EMBO J. 2:419-426, reported the utilization of various polyadenylation sites by "transcript 7" (ORF3 of Barker R et al., supra) and ocs.

The nos gene encodes nopaline synthase (sequenced by Depicker A et al. (1982) J. Mol. Appl. Genet. 1:561-573). Shaw C H et al. (1984) Nucl. Acids Res. 12:7831-7846; and An G et al. (1986) Mol. Gen. Genet. 203:245-250, provide functional analyses of nos.

Ti and Ri plasmid genes outside of the T-DNA region include the vir genes, which when mutated result in an avirulent Ti plasmid. The vir genes function in trans, being capable of causing the transformation of plant cells with T-DNA of a different plasmid type and physically located on another plasmid. Such arrangements are known as binary systems and the T-DNA bearing plasmids are generally known as micro-Ti plasmids. Many binary systems are known to the art. T-DNA need not be on a plasmid to transform a plant cell; chromosomally located T-DNA is functional (Hoekema A et al. (1984) EMBO J. 3:2485-2490). Ti plasmid-determined characteristics have been reviewed by Merlo, supra (see especially Table 11), and Ream and Gordon, supra.

Foreign Gene Expression

A gene encoding bean phaseolin has been transferred into and expressed in sunflower tumors. Transcription started and stopped at the correct positions, and introns were posttranscriptionally processed properly (Murai N et al. (1983) Science 222:476-482). The phaseolin gene was expressed at a high level in developing tobacco seeds (SenguptaGopalan C et al. (1985) Proc. Natl. Acad. Sci. USA 82:3320-3324). Similar results have been observed with a homologous gene, soybean betaconglycinin (Beachy R N et al. (1985) EMBO J. 4:3047-3053). Some genes for the endosperm protein zein, from the monocot *Zea mays,* are transcribed in dicot cells, though translational products of these transcripts has not been detected (Matzke M A et al. (1984) EMBO J. 3:1525-1531; Goldsbrough et (1986) Mol. Gen. Genet. 202:374-381).

Expression of RuBP-Case small subunit genes is light-regulated and developmentally regulated in transformed cells; the small subunit protein produced is correctly processed and sequestered within chloroplasts (Broglie R et al. (1984) Science 224:838-843; Fluhr R and Chua N H (1986) Proc. Natl. Acad. Sci. USA 83:2358-2362). Sequences involved in this light-inducibility and those needed for maximal expression have been identified (Morelli G et al. (1985) Nature 315:200-204; Nagy F et al. (1985) EMBO J. 4:3063-3068; Timko M P et al. (1985) Nature 318:579-582; Fluhr R et al. (1986) Science 232:1106-1112). Expression of transformed chlorophyll a/b binding protein genes is light-regulated and organ-specific in transformed tobacco plants (Lamppa G et al (1985) Nature 316:750-752).

A soybean heat shock gene is thermoinducible in sunflower tissue (Schoffl F and Baumann G (1985) EMBO J. 4:1119-1124). (A *Drosophila melanogaster* heat shock promoter is similarly functional in tobacco tissue (Spena A et al. (1985) EMBO J. 4:2739-2743).)

Chimeric Genes Having T-DNA Promoters

The nos promoter can drive expression of drug resistance structural genes useful for selection of transformed plant cells. Many resistance genes have been created for drugs including kanamycin, methotrexate, chloramphenicol, and hygromycin B. Helmer G et al., (1984) Biotechnol. 2:520-527, have created a fusion gene useful as a screenable marker having the promoter and 5'-end of the nos structural gene fused to *E. coli* *beta*galactosidase (lacZ) sequences. A chimeric nos/-kanamycin gene was functional (An G et al (1985) EMBO J. 4:277-284).

Murai N et al., (1983) Science 222:476-482, reported fusion of the ocs promoter and its structural gene's 5'-end to a phaseolin structural gene, and expression thereof. An ocs/hygromycin B resistance fusion protein gene has been created and is functional (Waldron C et al. (1985) Plant Mol. Biol. 5:103-108). An ocs-driven glyphosate gene has been constructed (Comai L et al. (1985) Nature 317:741-744).

Promoters for octopine $T_L$ genes ORF24 and ORF25 can also drive structural gene expression (Velten J et al. (1984) EMBO J. 3:2723-2730; Velten J and Schell J (1985) Nucl. Acids Res. 13:6981-6998; Gelvin SB et al. (1985) Mol. Gen. Genet. 199:240-248; Comai L et al. (1985) Nature 317:741-744).

Chimeric Genes Having Plant Promoters

An RuBP-Case small subunit promoter confers light-inducible expression in callus to chloramphenicol and kanamycin resistance genes (Herrera-Estrella L et al. (1984) Nature 310:115-120; Facciotti D et al. (1985) Biotechnol. 3:241-246; Simpson J et al. (1986) Science 233:34-38; Fluhr R et al. (1986) Science 232:1106-1112). A chalcone synthase promoter also drove light-inducible expression of a kanamycin resistance gene (Kaulen H et al. (1986) EMBO J. 5:1-8). Chlorophyll a/b binding protein promoters have been used to drive expression of ocs and kanamycin resistance structural genes (Jones JDG et al. (1985) EMBO J. 4:2411-2418; Simpson J et al. (1985) EMBO J. 4:2723-2729; Simpson et al. (1986) supra). Nodule-specific expression of a chloramphenicol resistance structural gene under control of a leghemoglobin promoter has been observed in a transgenic legume (Jensen J S et al. (1986) Nature 321:669-674). Teeri T H et al. (1986) EMBO J. 5:1755-1760, disclose a scheme for the identification of plant promoters by T-DNA-mediated transcriptional fusions with a kanamycin resistance gene.

Chimeric Genes Having Viral Promoters

Kanamycin resistance genes under control of a cauliflower mosaic virus (CaMV) promoters were expressed in plant cells transformed by T-DNA (Koziel M G et al. (1984) J. Mol. Appl. Genet. 2:549-562; Balazs E et al. (1985) Gene 40:343-348; Pietrzak M (1986) Nucl. Acids Res. 14:5857-5868). A methotrexate resistance gene behind the CaMV 35S promoter conferred methotrexate resistance (Brisson N et al. (1984) Nature 310:51114 514). The 35S promoter has been used to express an enzyme which conferred herbicide tolerance to transgenic cells and plants (Shah D M et al. (1986) Science 233:478-481). Tobacco mosaic virus coat protein has been expressed in transformed tobacco tissue under control of a CaMV promoter (Bevan M W et al. (1985) EMBO J. 4:1921-1926; Abel PP et al. (1986) Science 232:738-743). Odell J T et al., (1985) Nature 313:810-812, have mapped sequences of the CaMV 35S promoter needed for transcription.

SUMMARY OF THE INVENTION

It is well known that most herbivores cannot synthesize all twenty of the amino acids used to make proteins. These amino acids, which must be supplied in the herbivore's diet, are referred to as "essential amino acids." For many species of mammals, the basic amino acids, e.g. lysine, and the sulfur-containing amino acids, e.g. methionine, are essential. As cereal seed storage proteins are low in basic amino acids and legume storage proteins are low in sulfur-containing amino acids, mammalian diets often contain a mixture of legumes and grains so that the total amino acid complement consumed is balanced. The ability to express a monocot seed storage protein having relatively high levels of methionine, such as zein, in a dicot can allow one to create a more nutritious legume having a better mix of amino acids. In particular, the 15 kD variant of zein is useful, having over 15 mole % sulfur-containing amino acids. Therefore, it is an object of the present invention to express a monocot seed storage protein in a dicot. Methods are provided for expression of monocot genes in dicot cells. Dicot transcription controlling sequences/monocot seed storage protein gene combinations are also provided. Furthermore, DNA molecules useful for this are provided. As exemplified herein, an endosperm protein of *Zea mays,* the prolamine (ethanol soluble protein) zein, has been expressed in seeds of *Nicotiana tabacum.*

I have found it possible to produce a dicot cell containing a monocot seed storage protein. As exemplified herein, the dicot cell is of the family Solanaceae and of the genus Nicotiana, the monocot protein is from the family Gramineae and from the genus Zea; the protein is a prolamine, zein, having a molecular weight of 15 kD (kilodaltons). This protein can be present in dicot cells at a level greater than about 0.05% total protein including a level about or greater than 1.0% total protein. A plant, plant tissue, plant organ, or seed descended from or containing the monocot seed storage protein can also be produced. To obtain cells containing this monocot protein I have made DNA molecules having a non-monocot promoter and a monocot seed storage protein structural gene, the promoter and the structural gene being in such position and orientation with respect to one another that the structural gene is expressible in a dicot cell under control of the promoter. As exemplified herein, the promoter is a dicot promoter, more specifically is a seed storage protein promoter, and in particular a phaseolin promoter. As exemplified herein the monocot protein is from the family Gramineae and in particular is from the genus Zea. As exemplified herein the protein is a 15 kD prolamine, zein. This DNA also includes a transcript terminator, the promoter, the structural gene, and the transcript terminator being in such position and orientation with respect to one another that the structural gene is expressible in a dicot cell under control of the promoter and the transcript terminator. As exemplified herein the transcript terminator is a dicot polyadenylation site, in particular a phaseolin polyadenylation site. The dicot-expressible monocot seed storage protein gene can be combined with a T-DNA border sequence in the form of a micro-Ti plasmid. This micro-Ti plasmid can include a selectable or screenable marker that is expressible in a plant cell, e.g. neomycin phosphotransferase. After transformation into a dicot cell and integration into that cell's genome, this DNA will be flanked by dicot DNA that is not naturally contiguous with any dicot-derived components of the promoter/structural gene/transcript terminator combination. This combination flanked with genomic dicot sequences, these genomic sequences being not naturally contiguous with any dicot sequences that are part of the combination, is contained by a dicot cell, as exemplified herein by a cell of the family Solanaceae, more specifically a cell of the genus Nicotiana. A plant, plant tissue, plant organ, or seed may be descended from or contain this cell. These transformed cells can be produced by transforming a dicot cell to contain a DNA comprising a nonmonocot promoter and a monocot seed storage protein structural gene, the promoter and the structural gene being in such position and orientation with respect to each other that the structural gene is expressible under control of the promoter in the transformed dicot cell or in a cell descended from the transformed dicot cell. For example, this transformation can be accomplished by placing an Agrobacterium cell containing the DNA in contact with a dicot cell.

It is believed that before this invention there were no published reports of expression of a monocot seed storage protein structural gene in a dicot. Published reports indicated that zein structural genes under control of zein promoters could be transcribed in dicot cell; however, no translational products were detected. Interpretations of the published data include the possibility that zein protein was not stable in dicot cells or the possibility that zein-encoding mRNA could not be translated in dicot cells. Therefore, the discovery that insertion into dicot cells of this monocot seed storage protein structural gen under control of dicot transcription controlling sequences resulted in accumulation of the monocot seed storage protein was not expected.

DETAILED DESCRIPTION OF THE INVENTION

Figure 1:
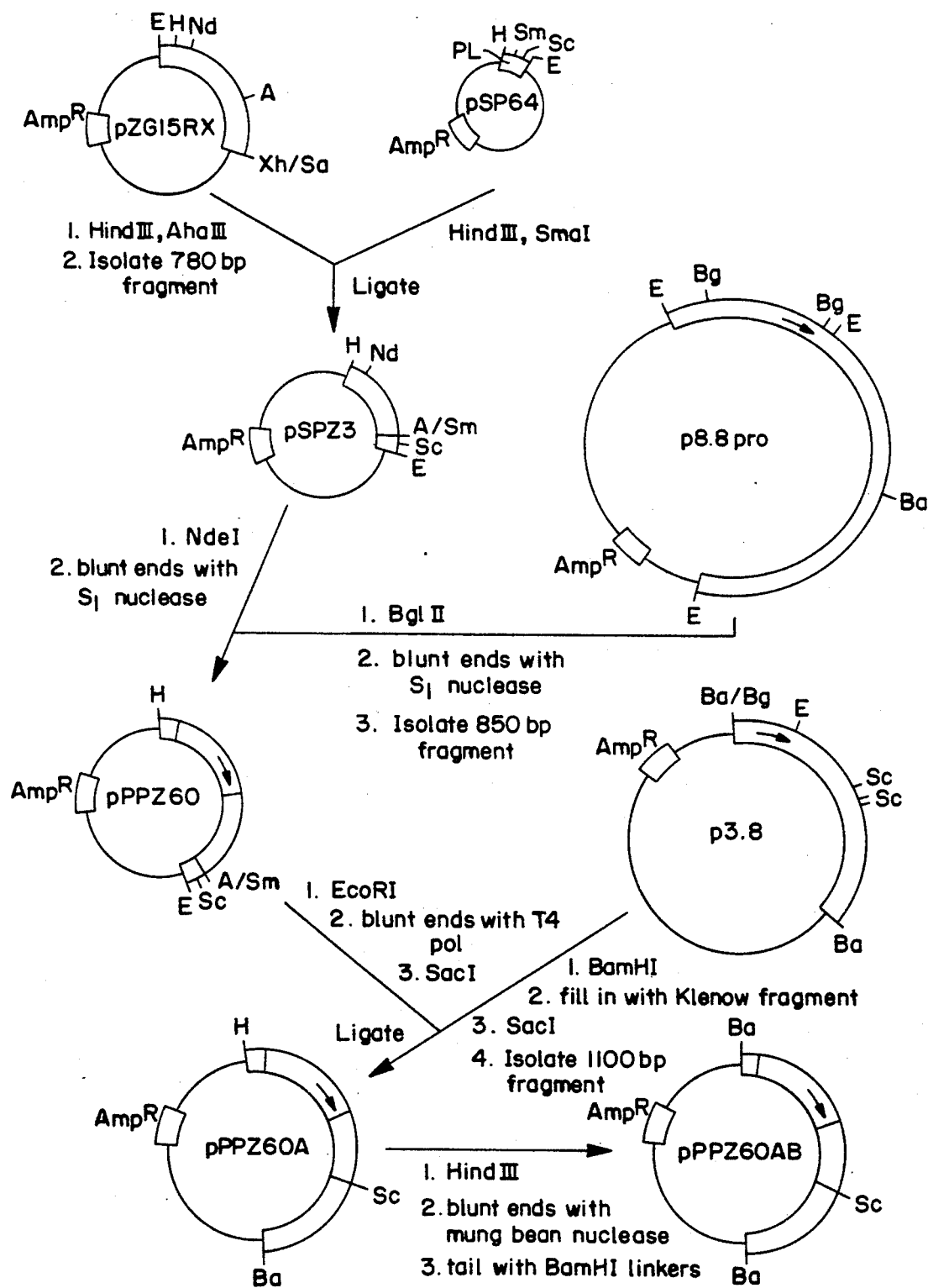
FIG. 1 diagrams, schematically and not necessarily to scale, insertion of a zein structural gene between phaseolin transcription controlling sequences. Restriction sites are abbreviated as follows: A, AhaI; Ba, BamHI; Bg, BglII; E, EcoRI; H, Hind III; Nd, NdeI; Sa, SalI; Sc, SacI; Sm, SmaI; and Xh, XhoI. Other abbreviations include Amp ® for a ampicillin resistance gene and PL for a polylinker (a short stretch of DNA having numerous restriction sites). The phaseolin promoter is indicated by an arrow within a curved box. Curved boxes represent locations of either the Amp ® gene, the PL (polylinker), and *P. vulgaris* and *Z. mays* sequences.

The following definitions are provided, in order to remove ambiguities to the intent or scope of their usage in the Specification and claims.

Promoter: Refers to sequences at the 5'-end of a structural gene involved in initiation of transcription. A plant-expressible promoter is any promoter capable of driving transcription in at least one type of plant cell in at least one developmental stage. Eukaryotic promoter sequences are commonly recognized by the presence of DNA sequences homologous to the canonical form 5' . . . TATAA . . . 3' about 10–30 base pairs (bp) 5'-to the location of the 5'-end of the mRNA (cap site). About 30 bp 5'-to the TATAA, another promoter sequence is often found which is recognized by the presence of DNA sequences homologous to the canonical form 5' . . . CCAAT . . . 3'.

Transcript Terminator: Refers herein to any nucleic acid sequence capable of determining the position of the 3'-end of a transcript. The transcript terminator DNA segment may itself be a composite of segments derived from a plurality of sources, naturally occurring or synthetic, prokaryotic, or eukaryotic, and may be from a genomic DNA or an mRNA-derived cDNA (mRNA: messenger RNA). Transcript termination sites include polyadenylation sites and sites determining the 3'-end of ribosomal RNAs (rRNAs), transfer RNAs (tRNAs), and nonpolyadenylated mRNAs (e.g. histone mRNA: Krieg PA and Melton DA (1984) Nature 308:203–206).

A polyadenylation site is a nucleic acid sequence correlated with polyadenylation of mRNA in eukaryotes, i.e. after transcriptional termination polyadenylic acid "tails" are added to the 3'-end of mRNA precursors. Polyadenylation sites are commonly recognized by the presence of homology to the canonical form 5' . . . AATAAA . . . 3', although variations of distance 5' to the 3'-end of the transcript, partial "read-through", and multiple tandem canonical sequences are not uncommon. DNA sequences between 20 and 35 bp downstream from the transcripts 3'-end seem to be necessary (McDevitt MA et al. (1984) Cell 37:993–999). It should be recognized that a canonical "polyadenylation site" may actually determine the location of the 3'-end of the mRNA and not polyadenylation per se (Proudfoot N (1984) Nature 307:412–413; Birnstiel ML et al. (1985) Cell 41 349–359).

Transcription Controlling Sequences: Refers to a promoter/transcript terminator site combination flanking a structural gene. The promoter and terminator DNA sequences flanking a particular foreign structural gene need not be derived from the same source genes (e.g. pairing two different T-DNA transcripts) or the same taxonomic source (e.g. pairing sequences from T-DNA with sequences from non-T-DNA sources such as plants, animals, fungi, yeasts, eukaryotic viruses, bacteria, and synthetic sequences).

Translational Initiation Site: Refers herein to the 5'AUg 3' translational start codon at the 5'-end of a structural gene, the nucleotide following the AUG, and the 3 nucleotides preceding the AUG (see Kozak M (1983) Microbiol. Rev. 47:1–45, and Kozak M (1984) Nucl. Acids Res. 12:857–872).

5'-Untranslated Sequence: Refers herein to the part of an mRNA between its 5'-end, or "cap site," and the translational start codon.

3'-Untranslated Sequence: Refers herein to the part of an mRNA between its translational stop codon and either its polyadenlylic acid segment or the 3'-end of a nonpolyadenylated mRNA.

Plant-Expressible Selectable or Screenable Marker: Refers herein to a genetic marker functional in a plant cell. A selectable marker (e.g. a kanamycin resistance gene) allows cells containing and expressing that marker to grow under conditions unfavorable to growth of cells not expressing that marker. A screenable marker (e.g. a beta-galactosidase gene) facilitates identification of cells which express that marker.

Dicot-Expressible: Refers to the ability of a gene to be expressed in a dicot cell.

Seed Storage Protein: Is a term well known in the art that refers to protein present in a seed having as its primary function the storage of amino acids for use by a seedling after germination to make other proteins.

T-DNA: Refers in the art to a DNA sequence, between and including two T-DNA border repeats, capable of being transferred from a vir genecontaining Agrobacterium cell to a plant cell and of being incorporated into the genome thereof.

Transforming: Refers to the act of causing a cell to contain a nucleic acid molecule or sequence not originally part of that cell.

Plant Tissue: Includes differentiated and undifferentiated tissues of plants including but not limited to roots, shoots, pollen, seeds, tumor tissue, such as crown galls, and various forms of aggregations of plant cells in culture, such as embryos and calluses. The plant tissue may be in planta or in organ, tissue, or cell culture.

Plant Cell: As used herein includes plant cells in planta and plant cells and protoplasts in culture.

The following terms are well known in the art and are not specifically or specially defined herein: prolamine, zein, phaseolin, T-DNA border repeat, transcription under control of a promoter, and structural gene.

Production of a genetically modified dicot cell expressing a monocot seed storage protein structural gene combines the specific teachings of the present disclosure with a variety of techniques and expedients known in the art. In most instances, alternative expedients exist for each stage of the overall process. The choice of expedients depends on variables such as the choice of the particular promoter, the particular structural gene, in many cases the particular transcript terminator, the exact locations of the sutures between the promoter, the structural gene, and the transcript terminator, the dicot species to be modified, the basic vector system for the introduction and stable maintenance of the promoter/structural gene combination, and the like, all of which present alternative process steps which those of ordinary skill are able to select and use to achieve a desired result. As novel means are developed for the stable insertion and transcription of foreign DNA in plant cells, those of ordinary skill in the art will be able to select among those alternate process steps to achieve a desired result. The fundamental aspects of the invention are the nature of the nonmonocot promoter/monocot seed storage protein structural gene combination and its use to synthesize the encoded storage protein in cells of plants transformed therewith. Other aspects include the nature and structure of the promoter/structural gene sequence and its means of insertion and expression in a plant genome. The remaining steps of the preferred embodiment for obtaining a genetically modified plant include inserting the combination into T-DNA, transferring the modified T-DNA to a plant cell wherein the modified T-DNA becomes stably integrated as part of the plant cell genome, techniques for in vitro culture and eventual regeneration into whole plants, which may include steps for selecting and detecting transformed plant cells and steps of transferring the introduced gene combination from the originally transformed strain into commercially acceptable cultivars, and monitoring expression in transformed plants.

A principal feature of the present invention in its preferred embodiment is the construction of a T-DNA derivative having an inserted gene under control of dicot-expressible transcription controlling sequences, i.e., between a promoter and a transcript terminator, as these terms have been defined, supra. The structural gene must be inserted in correct position and orientation with respect to the promoter. Position relates to which side of the promoter the structural gene is inserted. It is known that the majority of promoters control initiation of transcription and translation in one direction only along the DNA. The region of DNA lying under promoter control is said to lie "downstream" or alternatively "behind" or "3' to" the promoter. Therefore, to be controlled by the promoter, the correct position of a structural gene insertion must be "downstream" from the promoter. Orientation refers to the directionality of the structural gene. That portion of a structural gene which encodes the amino terminus of a protein is termed the 5'-end of the structural gene, while that end which encodes amino acids near the carboxyl end of the protein is termed the 3'-end of the structural gene. Correct orientation of the structural gene is with the 5'-end thereof proximal to the promoter. Similarly to the promoter region, the transcript terminator must be located in correct position and orientation relative to the structural gene being proximal to the 3'-end of the structural gene. Differences in rates of gene expression or developmental control may be observed depending on the particular components, e.g. promoters, transcript terminators, flanking DNA sequences, or site of insertion into the transformed plant's genome. Storage protein accumulation may also be affected by storage protein mRNA stability, which can be greatly infuenced by mRNA secondary structure, especially stem-loop structures. Different properties, including, but not limited to, such properties as stability, intracellular localization, posttranscriptional processing, and other functional properties of the expressed structural gene itself may be observed when promoter/structural gene/transcript terminator components are varied. All of these variations present numerous opportunities to manipulate and control the functional properties of the monocot seed storage protein, depending upon the desired physiological properties within the plant cell, plant tissue, and whole plant.

The fundamental principle of the present invention is that monocot seed storage proteins are capable of being made in dicot cells that contain a nonmonocot promoter/monocot seed storage protein structural gene combination. The requirements for which DNA sequence segments are to be included in a promoter/structural gene combination are best couched in functional terms. Transcript terminators, in particular polyadenylation sites, and promoters are understood in the art to be functional terms. Canonical sequences thereof are discussed above. However, the art understands a promoter to be that DNA segment capable of initiating transcription. Numerous promoters have been defined by methods such as deletion analysis. A promoter is the smallest continuous DNA segment that is necessary and sufficient to cause RNA polymerase to transcribe a flanking DNA segment. A promoter-bearing DNA segment may contain additional DNA sequences that are not necessary for transcription. Similarly, a polyadenylation site (or other transcript terminator) is functionally defined as the smallest continuous DNA segment that is necessary and sufficient to cause a transcript to become polyadenylated (or otherwise terminated). The functional requirements for a structural gene are also well understood. A structural gene must start with a translational initiation (start) site (AUG), end with a translational termination (stop) codon (UAA, UAG, or UGA) and have a integral number of triplet codons in-between, without an intervening stop codon.

The transcript of the dicot promoter/monocot structural gene may include nonmonocot sequences in addition to monocot sequences. Usually these nonmonocot sequences will be at the 5'- and 3'-ends of the mRNA. Often these nonmonocot components will be derived from promoter or transcript terminator DNA segments. As exemplified herein, the zeinencoding transcript probably has both its 5'- and 3'-ends donated from phaseolin mRNA 5'- and 3'ends. Inclusion of various nonmonocot sequences may affect mRNA stability, cellular localization of the mRNA, posttranscriptional processing, and the like. It is known to the art that RNA stability is affected by terminal structures such as 5'-capping and 3'-polyadenylation and by the extent of internal structure, i.e. intramolecular basepairing. Translational efficiency can similarly be affected by structures in the 5'-untranslated region, and by the exact sequence of the translational initiation site. An intron may be included in a monocot mRNA, provided that, if the splice sites are derived from two different genes, the intron splice sites be compatible.

Combining of DNA segments, including coding, promoter, and transcript terminator sequences, to form a promoter/structural gene/terminator combination is accomplished by means known and understood by those of ordinary skill in the art of recombinant DNA technology. Choice of promoter depends on the developmental regulation desired. Use of developmentally regulated promoters for gene expression in plants is described in the Background. T-DNA or CaMV promoters are advantageous as they are constitutive. The RuBP-Case small subunit promoter may be useful for expression in the green tissues of a plant transformed to contain a nonmonocot promoter/monocot seed storage gene combination. The promoter of a dicot seed storage protein gene (e.g. phaseolin) can be used to express a monocot seed storage protein structural gene (e.g. zein) in dicot (e.g. *Nicotiana tobaccum*) seeds. In the preferred embodiments, the transcript terminator is a polyadenylation site. The plant gene source of the polyadenylation site is not crucial provided that the polyadenylation site, the promoter and the structural gene are compatible for transcription and posttranscriptional processing.

As will be apparent to those of ordinary skill in the art, the promoter/structural gene combination may be placed between any restriction sites convenient for removing the combination from the plasmid it is carried on and convenient for insertion into the plant transformation vector of choice. For example, location of the gene combination insertion site within T-DNA is not critical as long as the transfer function of sequences immediately surrounding the T-DNA borders are not disrupted, since in prior art studies these regions appear to be essential for insertion of the modified T-DNA into the plant genome. The combination is inserted into the plant transformation vector by standard techniques well known to those skilled in the art. The orientation of the assembled promoter/structural gene combination, with respect to the direction of transcription and translation of endogenous vector genes is not usually critical; generally, either of the two possible orientations is functional.

As is well known in the art, T-DNA of micro-Ti plasmids can be transferred from an Agrobacterium strain to a plant cell provided the Agrobacterium strain contains certain trans-acting genes whose function is to promote the transfer of T-DNA to a plant cell. Micro-Ti plasmids are advantageous in that they are small and relatively easy to manipulate directly, eliminating the need to transfer the gene to T-DNA from a shuttle vector by homologous recombination. After the desired promoter/structural gene combination has been inserted, they can easily be introduced directly into an Agrobacterium cell containing trans-acting vir genes, the vir genes usually being on a "helper plasmid", that promotes T-DNA transfer. Introduction into an Agrobacterium strain is conveniently accomplished either by transformation of the Agrobacterium strain or by conjugal transfer from a donor bacterial cell, the techniques for which are well known to those of ordinary skill. For purpose of introduction of novel DNA sequences into a plant genome, Ti plasmids, Ri plasmids, micro-Ti plasmids, and T-DNA integrated into chromosomes should be considered functionally equivalent.

T-DNA having a promoter/structural gene combination can be transferred to plant cells by any technique known in the art. For example, this transfer is most conveniently accomplished by cocultivation of the Agrobacterium strain with plant cells or with plant tissues. Using these methods, a certain proportion of the plant cells are transformed, that is to say have T-DNA transferred therein and inserted in the plant cell genome. In either case, the transformed cells must be selected or screened to distinguish them from untransformed cells. Selection is most readily accomplished by providing a selectable marker or screenable marker incorporated into the T-DNA in addition to the gene combination. Examples of artificial markers include those reviewed in the Background (see the sections on Chimeric Genes). In addition, the T-DNA provides endogenous markers such as gene(s) controlling abnormal morphology of Ri-induced tumor roots and gene(s) that control resistance to toxic compounds such as amino acid analogs, such resistance being provided by an opine synthesizing enzyme (e.g. ocs). Screening methods well known to those skilled in the art include, but are not limited to, assays for opine production, specific hybridization to characteristic nucleic acid sequences (e.g. storage protein mRNA or T-DNA) or immunological assays for specific proteins (e.g. zein or neomycin phosphotransferase II).

Although the preferred embodiments involve use of micro-Ti plasmids, other T-DNA-based vector systems known to the art may readily be substituted. Furthermore, though the preferred embodiment of this invention incorporates a T-DNA-based Agrobacterium-mediated system for incorporation of the nonmonocot promoter/monocot seed storage protein structural gene into the genome of the plant which is to be transformed, other means for transferring and incorporating the promoter/structural gene combination are also included within the scope of this invention. Other means for the stable incorporation of the gene combination into a plant genome additionally include, but are not limited to, use of vectors based upon viral genomes, minichromosomes, transposons, and homologous or nonhomologous recombination into plant chromosomes. Alternate forms of delivery of these vectors into a plant cell additionally include, but are not limited to, fusion with vector-containing liposomes or bacterial spheroplasts, microinjection, encapsidation in viral coat protein followed by an infection-like process, and direct uptake of DNA, possibly after induction of plasmalemma permeability by an electric pulse, a laser, or a chemical agent. Means for transient incorporation and/or expression are also included within the scope of this invention. Systems based on Agrobacterium cells and T-DNAs can be used to transform angiosperms, including dicots and monocots, by transfer of DNA from a bacterium to a plant cell; systems based on alternate vectors or means for vector delivery may be used to transform gymnosperms and angiosperms.

Regeneration of transformed cells and tissues is accomplished by known techniques. An object of the regeneration step is to obtain a whole plant that grows and reproduces normally but which retains integrated T-DNA. The techniques of regeneration vary somewhat according to principles known in the art, and may depend upon the plant transformation vector and the species of the transformed plant. Regeneration of transformed tobacco plants, petunia plants, and plants of related species is well known to the art. As means for regeneration of other plant species are developed, the art will understand, without undue experimentation, how to adapt these newly discovered means for regeneration of plants from transformed plant cells and transformed plant tissues.

The genotype of the plant tissue transformed is often chosen for the ease with which its cells can be grown and regenerated in in vitro culture and for susceptibility to the selective agent to be used. Should a cultivar of agronomic interest be unsuitable for these manipulations, a more amenable variety is first transformed. After regeneration, the newly introduced promoter/structural gene combination may be readily transferred to the desired agronomic cultivar by techniques well known to those skilled in the arts of plant breeding and plant genetics. Sexual crosses of transformed plants with the agronomic cultivars yield initial hybrids. These hybrids can then be back-crossed with plants of the desired genetic background. Progeny are screened and/or selected for the continued presence of integrated promoter/structural gene combination, T-DNA, or for a new phenotype resulting from expression of the gene combination or other genes carried by the inserted DNA. In this manner, after a number of rounds of back-crossing and selection, plants can be produced having a genotype essentially identical to the agronomically desired parents with the addition of inserted DNA sequences.

EXAMPLES

The following Examples are presented for the purpose of illustrating specific embodiments within the scope of the present invention without limiting the scope, the scope being defined by the claims. Numerous variations will be readily apparent to those of ordinary skill in the art.

The Examples utilize many techniques well known and accessible to those skilled in the arts of molecular biology and manipulation of T-DNA and Agrobacterium; such methods are fully described in one or more of the cited references if not described in detail herein. All references cited in this Specification are hereby incorporated by reference. Enzymes are obtained from commerical sources and are used according to the vendors' recommendations and other variations known to the art. Reagents, buffers, and culture conditions are also known to those in the art. Reference works containing such standard techniques include the following: Wu R, ed. (1979) Meth. Enzymol. 68: Wu R et al., eds. (1983) Meth. Enzymol. 100 and 101: Grossman L and Moldave K, eds. (1980) Meth. Enzymol. 65; Weissbach A and Weissbach H, eds. (1986) Meth. Enzymol. 118 (see especially Rogers S G et al., pp. 627-640); Miller J H (1972) *Experiments in Molecular Genetics;* Davis R et al. (1980) *Advanced Bacterial Genetics;* Schleif R F and Wensink P C (1982) *Practical Methods in Molecular Biology:* Walker J M and Gaastra W, eds. (1983) *Techniques in Molecular Biology;* and Maniatis T et al. (1982) *Molecular Cloning.* Additionally, Lathe R F et al., (1983) Genet. Engin. 4:1-56, make useful comments on DNA manipulations.

Textual use of the name of a restriction endonuclease in isolation, e.g. "BclI," refers to use of that enzyme in an enzymatic digestion, except in a diagram where it can refer to the site of a sequence susceptible to action of that enzyme, e.g. a restriction site. In the text, restriction sites are indicated by the additional use of the word "site," e.g. "BclI sites." The additional use of the word "fragment," e.g. "BclI fragment," indicates a linear double-stranded DNA molecule having ends generated by action of the named enzyme (e.g., a restriction fragment). A phrase such as "BclI/SmaI fragment" indicates that the restriction fragment was generated by the action of two different enzymes, here BclI and SmaI, the two ends resulting from the action of different enzymes.

Plasmids, and only plasmids, are prefaced with a "p," e.g., pTi15955 or pH400, and strain designations parenthetically indicate a plasmid harbored within, e.g., *A. tumefaciens* (pTi15955) or *E. coli* H802 (pH400). The following strains have been deposited:

| E. coli K802 (pCT29K-2) | NRRL B-18010 |
| A. tumefaciens (pTi15955) | ATCC 15955 |
| E. coli HB101 (p8.8) | NRRL B-15393 |
| E. coli HB101 (p3.8) | NRRL B-15392 |

(ATCC American Type Culture Collection, 12301 Parklawn Dr., Rockville, M.D. 20852 USA; NRRL: ARS Patent Collection, Northern Regional Research Center, 1815 N. University St., Peoria, Ill. 61614 USA.) Other plasmids and strains are widely available and accessible to those in the art.

Example 1: Construction of a micro-Ti plasmid, pH575

E. coli K802 (pCT29K-2), which has been deposited as NRRL B-18010, was disclosed by Sutton D W et al., U.S. patent application Ser. No. 788,984, filed Oct. 21, 1985, now abandoned, which is hereby incorporated by reference. The T-DNA of pCT29K-2 can be represented as follows:

borderA . . . bacteria-selectable NPT1 . . . unique BglII site . . .

-continued plant-selectable NPT2 ... 5'-end of tml ... ocs ... border B.

Except for NPT1 (NPT1 is neomycin phosphotransferase I, NPT2 is neomycin phosphotransferase 11), all of these genes are transcribed in the same direction. This T-DNA can be removed from pCT29K-2 on a 9.52 kbp HindIII fragment.

Figure 2:
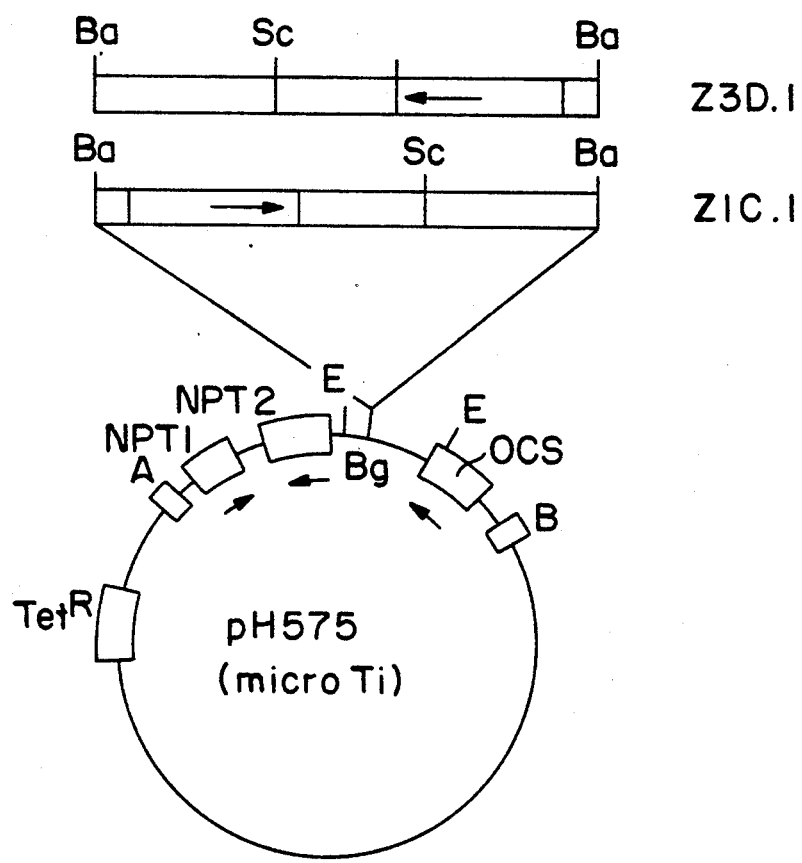
FIG. 2 diagrams, schematically and not necessarily to scale, various micro-Ti plasmids. Restriction sites are designated as in FIG. 1. Other abbreviations include A and B for the octopine-type T$_L$-DNA border repeats A and B, Tet ® for a bacteria-expressible tetracycline resistance gene, NPT1 for a bacterial expressible neomycin phosphotransferase I gene, NPT2 for a plant-expressible neomycin phosphotransferase II gene, and OCS for a plant-expressible octopine synthase gene (ocs). The curved boxes indicate the location of the Tet ®, NPT1, NPT2, and ocs genes, and the A and B border repeats. Arrows below the curved boxes indicate the direction of a gene's transcription while the arrow within the straight box indicates the location and direction of transcription of a phaseolin promoter.

The micro-T-DNA-carrying 9.52 kbp HindIII fragment of pCT29K-2 was mixed with and ligated to HindIII-linearized, dephosphorylated pTJS75 DNA (see Klee H J et al. (1985) Biotechnol. 3:637–642). Restriction mapping of E. coli transformants resistant both to kanamycin and to tetracycline resulted in identification of a colony harboring a plasmid designated pH575 (FIG. 2).

Example 2: Preparation of a phaseolin promoter p8.8 (designated pPVPh8.8 in FIG. 3 of Hall T C et al. (1983) in Structure and Function of Plant Genes, eds. Ciferri 0 and Dure L, pp. 123–142) is a subclone of lambda-177.4 (Sun S M et al. (1981) Nature 289:37–41). p8.8 was made by partial EcoRI digestion of lambda-177.4 and insertion of a 8.8 kbp fragment into EcoRI-linearized pBR322. E. coli HB101 (p8.8) is on deposit as NRRL B-15393. Though the work done herein was done with p8.8 and derivatives thereof, p3.8 (designated AG-pPVPh3.8 by Slightom J L et al. (1983) Proc. Natl. Acad. Sci. USA 80:1897–1901) could be substituted. E. coli HB101 (p3.8) is on deposit as NRRL B-15392.

Phaseolus DNA was removed from p8.8 and inserted into an M13-based vector suitable for oligonucleotide-directed, site-specific mutagenesis. Hybridization to an oligonucleotide having sequence 5'CATCATAG-TAGATCTAGTATTGAATATGAG', the two underlined bases representing a mutation relative to the sequence of the Phaseolus DNA. This substitutes GA for the C present at position +71 as reckoned by Slightom et al., supra., thereby creating a BglII site. Then the site specific mutagenesis procedure was completed, a mutated M13-derivative was identified, and the mutated Phaseolus DNA was reinserted into pBR322, thereby producing a plasmid designated p8.8pro, having a BglII site present about 8 bp 5'-to the phaseolin ATG translational start site. To summarize, p8.8pro differs from p8.8 as follows:

```
coordinate and coding        +71         MetMet...
p8.8       5'...CTCATATTCAATACTAC - TCTACTATGATG...3'
p8.8pro    5'...CTCATATTCAATACTAGATCTACTATGATG...3'
restriction site
                                 BglII
```

The phaseolin promoter can be removed from p8.8pro on a 0.85 kbp (kilobase pair) BamHI/BglII fragment, the BamHI site being 5'-to the new BglII site.

Example 3: Preparation of a zein structural gene

A plasmid designated herein as pZG15RX (FIG. 1) is an EcoRI/XhoI subclone in pBR322 of the genomic clone gZ15A. pZG15RX carries the left most EcoRI/XhoI fragment disclosed by FIG. 1 of Pedersen K et al. (1986) J. Biol. Chem. 261:6279–6284. gZ15A carries a 15 kD zein gene and was isolated and sequenced by Pedersen et al. pZG15RX DNA was digested with HindIII and AhaIII, which respectively cut at about positions -179 and 673, as numbered in FIG. 2 of Pedersen et al. A 0.75 kbp fragment carrying the zein structural gene was then electrophoretically isolated. This fragment was then mixed with and ligated to HindIII- and SmaI-digested, dephosphorylated, pSP64 (FIG. 1) DNA (Melton D A et al. (1984) Nucl. Acids Res. 12:7035–7056). The ligation mixture was transformed into E. coli MC1061, ampicillin-resistant transformants were screened by restriction analysis, and a colony was identified which harbored a plasmid, designated pSPZ3 (FIG. 1), having the 15 kD zein gene inserted into pSP64.

Example 4: Combination of a phaseolin promoter and a zein structural gene pSPZ3 DNA was digested with NdeI and $S_1$ nuclease, thereby converting the NdeI sticky-end to blunt-ends. p8.8pro (FIG. 1) DNA was digested with BglII, BglII sticky-ends were converted to blunt-ends with $S_1$ nuclease, and a 0.85 kbp fragment was isolated by acrylamide gel electrophoresis. This 0.85 kbp fragment, which carried a phaseolin promoter, was mixed with and ligated to the blunt-ended, linearized pSPZ3 DNA. After transformation into E. coli MC1061, DNA was isolated from ampicillin-resistant transformants. A colony was identified which harbored a plasmid, designated pPPZ60 (FIG. 1), having the phaseolin promoter and the zein structural gene in such position and orientation with respect to each other that in a plant cell a zein-encoding transcript can be transcribed under control of phaseolin promoter.

Example 5: Addition of a polyadenylation site

Though pPPZ60 has a zein-derived polyadenylic acid addition concensus sequence, it does not have extensive zein sequences 3'-to this concensus sequence. To assure proper polyadenylation, a more extensive phaseolin sequence which included a polyadenylation site was inserted behind the phaseolin promoter/zein structural gene combination. pPPZ60 DNA was digested with EcoRI. After having the EcoRI sticky-ends converted to blunt ends by incubation with T4 DNA polymerase, the linearized pPPZ60 DNA was digested with SacI, which, like EcoRI, cuts in the pSP64-derived polylinker 3'-to the promoter/structural gene combination. p3.8 (FIG. 1) DNA (Slightom et al., surpa) was cut with BamHI, had its BamHI sticky-ends converted to blunt-ends by incubation with the Klenow fragment of E. coli DNA polymerase I, and then, cut with SacI. A 1.1 kbp fragment carrying the phaseolin polyadenylation site was then electrophoretically isolated. This 1.1 kbp fragment was mixed with and ligated to the opened pPPZ60 DNA. After transformation into E. coli and selection for resistance to ampicillin, a colony was found harboring a plasmid, designated pPPZ60A (FIG. 1), having a phaseolin polyadenylation site 3'-to the promoter/structural gene combination in such position and orientation relative to the structural gene that in a plant cell a zein-encoding transcript can be transcribed under control of the phaseolin promoter and polyadenylation site. In pPPZ60A the SacI site between the zein and phaseolin polyadenylation sites was restored and BamHI 3'-to the phaseolin polyadenylation site was reconstructed.

The promoter/structural gene/polyadenylation site combination can be removed from pPPZ60A on a 2.8 kbp HindIII/BamHI fragment, the HindIII and BamHI sites being respectively 5'-to and 3'-to the combination. However, to insert the combination into the pH575 micro-Ti plasmid, it is useful to have the combination on a BamHI fragment. Therefore, the HindIII site was converted to a BamHI site. pPPZ60A DNA was digested with HindIII. This linearized, phosphorylated DNA was blunt-ended by digestion with mung bean nuclease. The blunt-ended pPPZ60A DNA was then mixed with and ligated to unphosphorylated BamHI linkers having a single-stranded sequence of 5'CGGGATCCCG3'. After transformation into *E. coli* MC1061, plasmid DNAs isolated from ampicillin-resistant transformants were characterized by restriction mapping. A colony was identified which harbored a plasmid, designated pPPZ60AB (FIG. 1), having a BamHI site replacing the pPPZ60A HindIII site.

Example 6: Insertion of the promoter/structural gene combination into pH575

BamHI-digested pPPZ60AB DNA was mixed with and ligated to BglII-digested, dephosphorylated pH575 (FIG. 2) DNA. The ligation mix was transformed into *E. coli* MC1061 and plasmid DNAs isolated from kanamycin-resistant transformants were characterized by hybridization with a $^{32}$P-labeled zein gene fragment. Colonies were identified which harbored plasmids, designated PH5PZIC and pH5PZ3D (FIG. 2), which had the promoter/structural gene combination antiparallel and parallel, respectively, to the ocs and kan genes of pH575.

Example 7: Plant transformation

PH5PZIC and pH5PZ3D were individually transferred into *A. tumefaciens* LBA4404 (Ooms G et al. (1981) Gene 14:33–50), a vir gene-harboring, microTi-mobilizing strain, by the triparental mating technique (Ruvkun GB and Ausubel FM (1981) Nature 289:85–88), which is well known in the art. Tobacco leaf tissue was obtained from 4- or 5-week old *Nicotiana tabacum* var. Xanthi$^{NC}$ plants grown in a greenhouse. Inoculation was by a modification of the method Horsch RB et al. (1985) Science 227:1229–1231. Inocula were prepared by placing two loopfuls of agrobacteria in 10 ml of L-broth. After suspension by forceful pipetting with a Pasteur pipet, inocula could be used immediately. Leaves were excised and midribs were removed; cutting surfaces were wetted with L-broth to help keep the leaves wet. Leaf pieces were about 2–4 mm wide and about 7–10 mm long. Leaf pieces were dipped in the inoculum for 5–10 min, though in some experiments, leaf pieces were just dipped into the inoculum or were infiltrated with the inoculum in a vacuum flask. Pieces were then blotted dry on sterile filter paper and placed upside-down on feeder plates prepared from a Xanthi suspension culture. The feeder plates had a SMPi medium (SMPi: MX− supplemented with 0.1 mg/l p-chlorophenoxyacetic acid (pCPA) and 7.5 mg/l 6−(8,8-dimethylallylamino)purine (2iP); MX−:1.65 g/l $NH_4NO_3$, 1.9 g/l $KNO_3$, 440 mg/l $CaCl_2.2H_2O$, 370 mg/l $MgSO_4.7H_2O$, 170 mg/l $KH_2PO_4$, 0.83 mg/l KI, 6.2 mg/l $H_3BO_3$, 22.3 mg/l $MnSO_4.4H_2O$, 8.6 mg/l $ZnSO_4.7H_2O$, 0.25 mg/l $Na_2MoO_4.2H_2O$, 0.025 mg/l $CuSO_4.5H_2O$, 0.025 mg/l $CoCl_2.6H_2O$, 1 g/l inositol, 50 mg/l nicotinic acid, 50 mg/l pyroxidine.HCl, 50 mg/l thiamine.HCl, 30 g/l sucrose, pH 5.8, solidified with 8 g/l agar). Leaf pieces were removed from feeder plates after 4–6 days and placed on SMPi medium supplemented with 500 mg/l carbenicillin, 50 mg/l cloxacillin, and 100–300 mg/l kanamycin (200 mg/l optimum). The resulting shoots were excised and placed on MX- medium supplemented with 100–300 mg/l kanamycin (200 mg/l optimum).

Example 8: Expression in plants

Regenerated tobacco plants descended from cells transformed by *A. tumefaciens* LBA4404 (pH5PZ1C) or *A. tumefaciens* LBA4404 (pH5PZ3D) were self-fertilized. The resulting seeds were germinated on MX− supplemented with 100–300 mg/l kanamycin (200 mg/l optimum) to select plants containing the nonmonocot promoter/monocot seed storage protein structural genebearing T-DNA. Presence of the transformed T-DNA was confirmed by Southern blot analysis. Presence of zein protein in developing tobacco seeds was detected by SDS-polyacrylamide gel electrophoresis (SDS-PAGE) followed by staining of the resultant gels, western blots (SDS-PAGE followed by transfer to membrane filters and immunological detection), and immuno-dot blots (immobilization of protein in dots on filter paper followed by immunological detection). Zein protein was detectable at levels over about 0.25 ng/seed or at about 0.05% protein, and many transformants had zein levels of 5 ng/seed or about 1% protein.

I claim:

1. A dicot cell containing a monocot seed storage protein, wherein said protein is a prolamine, wherein said prolamine is a zein.

2. A cell according to claim 1, wherein the protein is a 15 kD zein.

3. A cell according to claim 2, wherein the cell is a cell in a seed and wherein the protein is present at a level greater than or equal to about 0.05% total protein.

4. A cell according to claim 2, wherein the cell is a cell in a seed and wherein the protein is present at a level greater than or equal to about 1.0% total protein.

* * * * *